(12) United States Patent
Newman et al.

(10) Patent No.: US 11,969,328 B2
(45) Date of Patent: *Apr. 30, 2024

(54) TRANSDERMALLY POWERED MR-CONDITIONAL MEDICAL IMPLANT INFLATOR SYSTEM

(71) Applicant: MHN Biotech LLC, Chevy Chase, MD (US)

(72) Inventors: Howard S. Newman, Annapolis, MD (US); Marcel I. Horowitz, Chevy Chase, MD (US); Arthur L Burnett, Baltimore, MD (US)

(73) Assignee: MHN BIOTECH LLC., Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/095,451

(22) Filed: Jan. 10, 2023

(65) Prior Publication Data
US 2023/0157800 A1    May 25, 2023

Related U.S. Application Data

(63) Continuation of application No. 17/367,006, filed on Jul. 2, 2021, now Pat. No. 11,554,002, which is a continuation of application No. 15/971,312, filed on May 4, 2018, now Pat. No. 11,051,923, which is a continuation-in-part of application No. 15/153,382, filed on May 12, 2016, now Pat. No. 10,383,715.

(60) Provisional application No. 62/220,593, filed on Sep. 18, 2015.

(51) Int. Cl.
A61F 2/26    (2006.01)
A61F 2/00    (2006.01)

(52) U.S. Cl.
CPC .......... *A61F 2/004* (2013.01); *A61F 2/0054* (2013.01); *A61F 2/26* (2013.01); *A61F 2250/0002* (2013.01); *A61F 2250/003* (2013.01)

(58) Field of Classification Search
CPC .. A61M 31/00; A61M 31/002; A61M 60/122; A61M 60/126; A61M 60/165; A61M 60/80; A61M 60/81; A61F 5/005; A61F 5/0053; A61F 2/04
See application file for complete search history.

(56) References Cited

U.S. PATENT DOCUMENTS

| | | | | |
|---|---|---|---|---|
| 11,051,923 B2 * | 7/2021 | Newman | ............... | A61F 2/0054 |
| 2005/0277912 A1 * | 12/2005 | John | .................. | A61M 5/16827 604/890.1 |
| 2008/0286330 A1 * | 11/2008 | Shafer | .................... | C07K 16/18 424/423 |

* cited by examiner

*Primary Examiner* — Samuel G Gilbert
(74) *Attorney, Agent, or Firm* — HOGAN LOVELLS US LLP

(57) ABSTRACT

A wirelessly powered inflatable medical implant system includes a medical provider software application, a patient external controller and a MR-Conditional, nonferrous pump in reservoir implant. The medical provider software application programs the patient external controller for the patient to transmit wireless power and control signals to circuitry in a pump in reservoir implant. In response, the pump in reservoir implant, containing a fluid reservoir and pump package submerged therein, transfers fluid from the reservoir through tubing, and into one or more inflatable medical implants. Submerging the pump package within the reservoir simplifies surgery in males and pump placement in females and provides pump package heatsinking to limit implant overheating.

4 Claims, 9 Drawing Sheets

TRANSDERMALLY POWERED MR-CONDITIONAL MEDICAL IMPLANT INFLATOR SYSTEM

CROSS REFERENCE TO RELATED APPLICATIONS

This application is a continuation application of U.S. patent application Ser. No. 17/367,006, filed Jul. 2, 2021, which is a continuation of U.S. patent application Ser. No. 15/971,312, filed May 4, 2018, which is a continuation-in-part of U.S. patent application Ser. No. 15/153,382, filed on May 12, 2016, which claims priority to U.S. Provisional Application No. 62/220,593 filed on Sep. 18, 2015. The entire disclosures of the prior applications are hereby incorporated by reference.

FIELD OF THE INVENTION

The present invention is directed to an apparatus and method for treating erectile dysfunction, urinary and fecal incontinence, and other medical problems treatable with inflatable medical implants. In particular, the apparatus transmits sufficient transdermal power for its MR-Conditional pump in reservoir implant to inflate one or more inflatable medical implants without implanted batteries or other internal energy storage. Specifically, the apparatus consists of a medical provider software application for programming and monitoring the apparatus; a patient external controller with a power source and transdermal power transmitter; a pump in reservoir implant containing a submerged power receiver, a microcontroller, a nonferrous electric motor-pump-valve assembly and monitoring sensors; and a pressure relief tube should the pump in reservoir implant fail.

BACKGROUND OF THE INVENTION

Inflatable medical implants with manually operated pumps and reversing switches placed in the male scrotum or female labia, which transfer fluid back and forth between an abdominal reservoir and inflatable penile cylinders, urethra cuffs and anal cuffs, are known for treatment of erectile dysfunction, urinary incontinence and fecal incontinence. Some patients, particularly older people with arthritis, find it difficult to operate the implanted manual pump and reversing switch, and there is not a comfortable place to implant the pump in females. Therefore, many patients elect not to have treatment.

More recent concepts replace the implanted manual pump and reversing switch with an electrically driven pump which may be controlled and powered from an external source. In operation, an external unit sends energy and control signals wirelessly to an internal unit, which then activates a separately placed pump unit. Signals may also be fed back from the internal unit to the external unit to control energy flow.

In certain systems, external alternating current power is transmitted transdermally by close-coupled magnetic induction typically operating in the band from 100 KHz to 200 KHz and forming an air core electrical transformer with its primary winding external to the patient and its secondary winding internal to the patient. Due to the low permeability of air and body tissue, few magnetic flux linkages connect between these primary and secondary windings; not like in an iron core transformer where most of the magnetic flux is coupled between primary and secondary windings. Therefore the primary and secondary windings must be placed within a few millimeters of each other to safely transmit any appreciable power, which means the implanted transformer secondary may be implanted in the dermis, a physically and cosmetically uncomfortable situation.

In some systems, this placement problem is alleviated with an internal rechargeable battery or capacitor to accumulate enough energy over time from a magnetic induction source so that when needed, the pump gets enough power to transfer the required fluid. Other systems use high voltages to increase power transmission over longer distances, however increasing the transmitted voltage increases the risk of electric shock. In all these systems, the voltage induced in the internal secondary winding can vary widely due to the patient's placement of the external primary windings with respect to the implanted secondary winding.

Full-wave Schottky diode bridge rectifiers with electromagnetic interference filters are known to convert the secondary winding's varying alternating current voltage into varying direct current voltage. However these full-wave bridge rectifiers have two diode voltage drops in their current delivery path, which set a limit on their efficiency.

In many of these systems, one or more linear voltage regulators are used to convert the varying direct current voltage to stable direct current voltage to power the electronics and the motor. These linear voltage regulators waste transmitted energy and can generate significant heat in the implant.

Technology to limit linear voltage regulator inefficiency is known in the form of a transdermal voltage feedback loop which limits how much voltage is applied to the external primary winding and reaches the internal regulator through the secondary winding, and therefore limits how much power is transmitted and must be dissipated in the linear regulator. Other systems use switch mode power supplies, which can achieve 70-90% efficiency.

In some systems, brushed direct current and brushless direct current motors are known to drive the pump. Both brushed and brushless direct current motors have rotors and stators containing ferrous material and are MR-Unsafe. Brushed direct current motors may be connected to switch mode power supply's output though a solid state forward-off-reversing switch.

Brushless direct current motors are comprised of a direct current to 3-phase inverter and a 3-phase induction motor. Such inverters generate 3-phase pulse width modulated signals to drive a metal-oxide-semiconductor field-effect transistor 3-phase half control bridge circuit, which then feeds the motor.

Positive displacement rotating internal gear fluid pumps, which can be built in millimeter diameters, are also known. For submerged operation, such pumps use a hermetically sealed motor magnetically coupled to the pump to prevent fluid from entering the motor. This magnetic coupling is MR-Unsafe.

What is needed is a MR-Safe or MR-Conditional apparatus without reduction gears and with efficient power transmission and conversion, which will transmit enough power transdermally to inflate and deflate medical implants in less time and with greater efficiency, higher reliability, lower implant voltage, in a small implant volume and with minimal surgical impact for men by not involving the scrotum, and, especially for incontinent women, where there is not a comfortable place to implant a separate pump unit.

SUMMARY OF THE INVENTION

The present invention is directed to an apparatus and method for treating erectile dysfunction, urinary and fecal incontinence, and other medical problems treated with inflatable medical implants. In particular, the present disclosure relates to a MR-Safe or MR-Conditional apparatus that can transfer enough transdermal energy to power a nonferrous motor, fluid pump and valve combination submerged in a reservoir that is small enough to fit into a patient's abdomen and capable of inflating and deflating multiple inflatable medical implants, such as dual penile cylinders, anal cuffs and urethra cuffs, in a short amount of time. For example, the apparatus may inflate or deflate the medical implants in less than 45 seconds.

MR-safe means there are no MRI restrictions for a patient with such an implant. MR-Conditional means a patient with a MR-Conditional implant can have a MRI study conducted in specific MRI machines, such as 1.5-tesla MRI machines. The apparatus disclosed has an implant which is comprised of nonferrous motors, pumps and valves; however, the implant may contain electronic components or conductors which may be MR-Conditional.

The apparatus includes a medical provider software application, a patient external controller, and a MR-safe or MR-Conditional pump in reservoir implant. The medical provider software application, running on any computing device, such as a tablet, PC or MAC, allows the medical provider to individually program each patient's patient external controller for their personal use, to monitor each patient's pump in reservoir implant usage, and to perform statistical analysis of usage across patients. The medical provider software application communicates with the patient external controller via wired or wireless communications, such as Ethernet, radio, Wi-Fi or Bluetooth.

The patient external controller contains a rechargeable battery power source, such as a Lithium Ion battery; a patient display, such as a touch panel liquid crystal display, and control switches, such as pushbuttons; a microcontroller; a transdermal power transmitter which generates a high frequency, evanescent electromagnetic field from a power amplifier and resonant antenna; a bidirectional radio link with the pump in reservoir implant; and a bidirectional link with the medical provider software application.

In operation, the medical provider uses the medical provider software application to program the patient external controller for use by the specific patient. The patient then activates a control on the patient external controller to transmit control signals, data and power to the pump in reservoir implant to inflate or deflate one or more inflatable medical implants. The pump in reservoir implant sends performance data back to the patient external controller so the patient may monitor implant operation on the display. The patient external controller stores the data for later transmission back to the medical provider software application so the medical provider can monitor and, if necessary, update pump in reservoir implant operation.

The pump in reservoir implant includes a biocompatible case enclosing a reservoir containing an isotonic fluid, such as normal saline, which is pumped into and out of one or more inflatable medical implants to cause inflation and deflation. The fluid also acts as a heat sink for a submerged cylinder containing circular electronic circuit boards and a nonferrous pump assembly comprising a 3-phase squirrel cage motor, an internal gear pump, and one or more piezoelectric valves. The amount of fluid transferred by the pump may be controlled by powering the pumps for a fixed number of rotations or by pump output pressure.

One or more independently controlled piezoelectric valves achieve independent control of one or more inflatable medical implants to treat multiple medical problems and to prevent leakage through the pump. That is, when multiple medical implants are included, each medical implant is connected to a dedicated piezoelectric valve. A pressure relief tube, with its top under the dermis, is provided for deflation by the medical provider should the pump in reservoir implant fail.

Sensors in the pump in reservoir implant measure pumping parameters for optimizing pump performance and monitoring for implant failures. Sensor data may include reservoir and inflatable medical implant pressure, pump speed, motor current and voltage, temperature, leaks, and electrical shorts.

The data from the sensors is also sent to the patient external controller for monitoring by the patient and for storage for later analysis by the medical provider. The medical provider may then noninvasively change inflation parameters by reprogramming the patient external controller via the medical provider software application.

No power is stored internally in the pump in reservoir implant, so the implant is completely passive at all times except when powered by the patient external controller. A data link handshake and foreign object detection is provided to prevent the implant from being powered by the MRI machine's radio frequency transmitter or other sources, or for power to be transmitted to foreign objects.

DETAILED DESCRIPTION OF THE INVENTION

Figure 1:
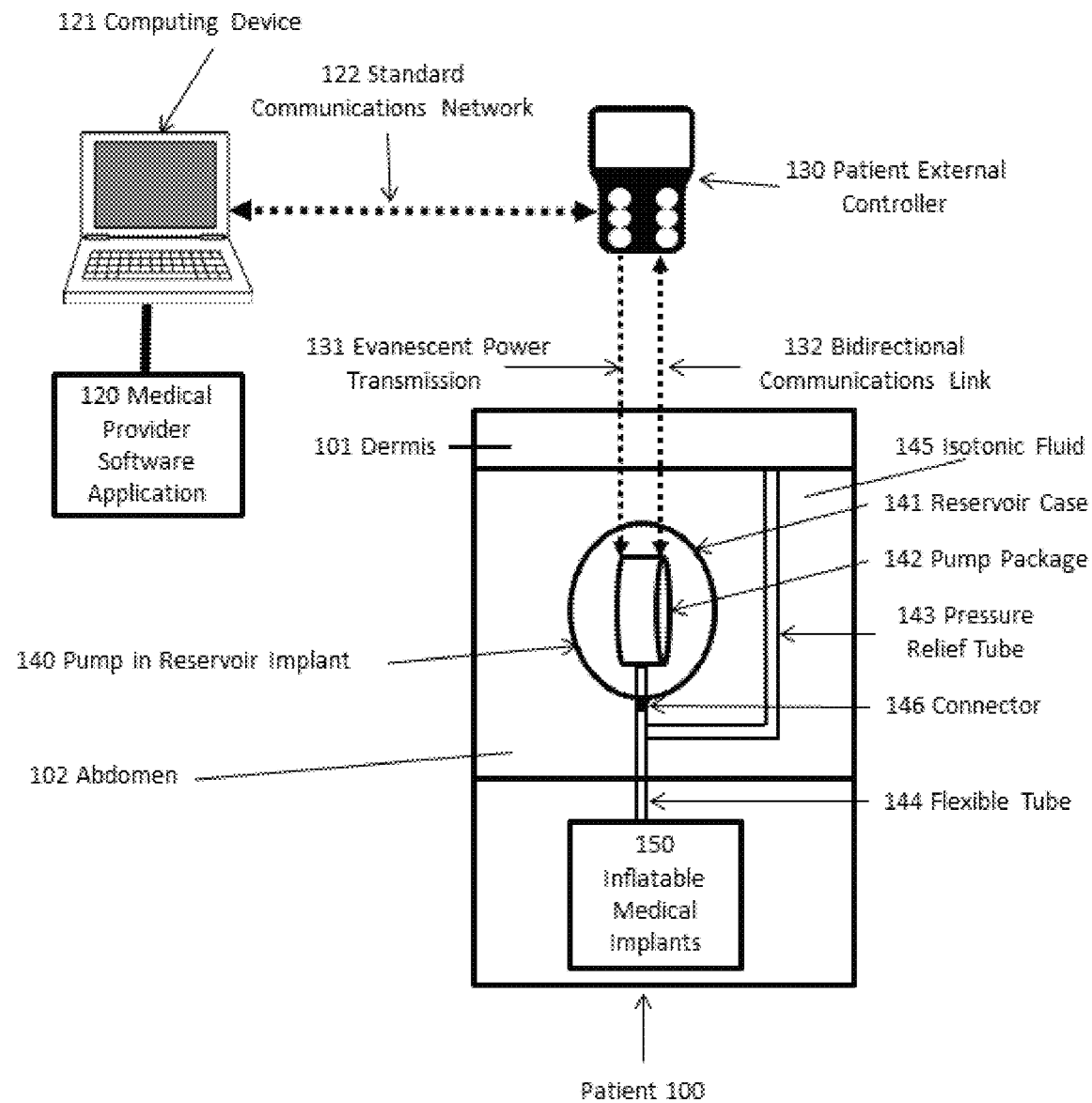
FIG. 1 is a diagram illustrating a transdermally powered MR-Conditional medical implant inflator system

The present invention is directed to an apparatus and method for treating erectile dysfunction, urinary and fecal incontinence and other conditions treated by inflatable medical implants. The apparatus includes an MR-Safe or MR-Conditional transdermally powered inflator for inflatable medical implants. As shown in FIG. 1, the apparatus includes a medical provider software application 120, a patient external controller 130, and a pump in reservoir implant 140, which can inflate and deflate one or more inflatable medical implants 150 in a short time period by transferring isotonic fluid at a particular or varying pressure. For example, the implants may be inflated or deflated in 45 second by transferring 60 milliliters of isotonic fluid at 25 pounds per square inch pressure.

The pump in reservoir implant 140 is surgically placed in a patient's 100 abdomen 102, and a flexible tube 144 is run from it to the inflatable medical implant 150. The pump in reservoir implant contains all the pumping components, which obviates the need for surgeons to enter the scrotum in males or providing uncomfortable pump locations in females. As shown in FIG. 1, a pressure relief tube 143 is placed in the abdomen 102 close to the dermis 101 for pump in reservoir implant 140 deflation by the medical provider should the apparatus fail.

The medical provider software application 120, executed on a computing device 121, such as a desktop, laptop, smartphone, or tablet, allows the medical provider to set, monitor and noninvasively change inflatable medical implant 150 inflation parameters stored in the patient external controller 130 for transmission to the pump in reservoir implant 140. Inflation parameters may originate from the medical provider, the apparatus provider or from performance data received from sensors placed in the pump in reservoir implant 140. The medical provider software application 120 also collects patient external controller 130 data from multiple patients so trends in usage and performance may be analyzed for determining settings and for scientific papers.

Figure 2:
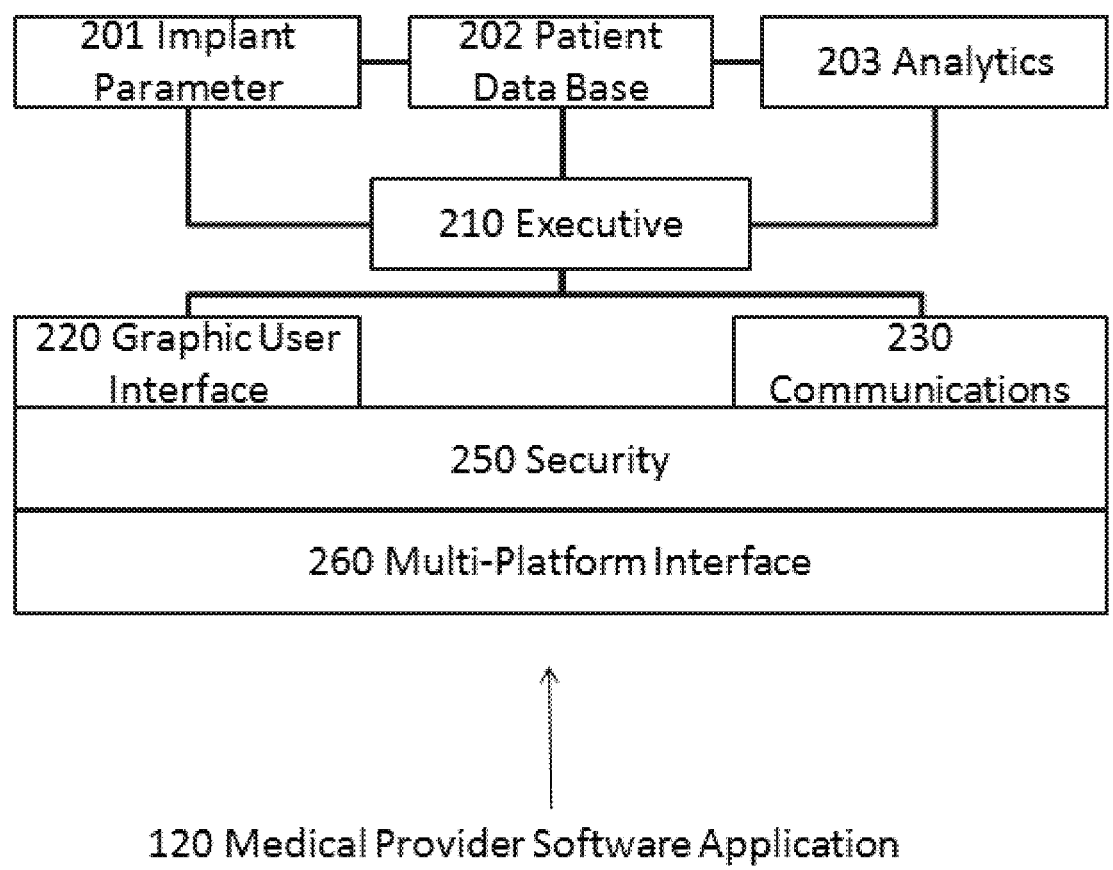
FIG. 2 is a bock diagram of the medical provider software application.

A block diagram of the software modules contained in the medical provider software application 120 is shown in FIG. 2. The implant parameter module 201 provides the medical provider with the capability to set and update the patient external controller's 130 software and inflation parameters, and to monitor implant operation. The medical provider may set parameters including the amount of fluid that the pump transfers and at what speed for inflation and deflation. The medical provider may set the amount of fluid and speed parameters as constant values, or may set the parameters to change depending on particular times of the day. For example, to increase anal and urinary artificial sphincter life, the medical provider may want to apply less pressure to the artificial sphincter at night, when less pressure is needed in supine patients, thereby reducing tissue wear. Pump operating time and output pressure data fed back to the module is then available to assist the medical provider in finding this minimum, and noninvasively adjusting it over time, as tissue atrophies.

Data from the implant parameter module 201 is stored in an encrypted patient data base module 202. The patient data base module 202 may store patient implant data for all the medical provider's patients. An analytics module 203 provides the medical provider with the capability to study trends in patient data contained in the patient data base 202. Analysis may include looking at atrophy rates of artificial sphincter patients with specific devices, and warning that a particular device is about to fail.

An executive module 210 controls and oversees the use of other modules by providing services such as such a logon, logoff and module selection. A graphic user interface module 220 provides the displays and controls for the medical provider to interface with the application's modules.

When in range, such as during office visits or hospitalizations, a communications module 230 provides for computer instructions and data transfer between the medical provider software application 120 and the patient external controller 130 using encrypted transmissions over a standard communications network 122, such as Ethernet, USB drive, Bluetooth or Wi-Fi, as shown in FIG. 1. The communications module 230 may also retrieve implant performance data stored in the patient external controller 130. A security module 250 provides data encryption and medical provider authentication. And, a multiplatform interface module 260 provides application operation across different medical provider computing devices 121 with different screen sizes. All module software may be updated from time to time by the apparatus provider via disk and over the internet.

A patient external controller 130, in communication with the medical provider software application 120 and the pump in reservoir implant 140, receives and stores inflation data and computer instruction updates from the medical provider software application 120, and sends data, power and computer instructions to the pump in reservoir implant 140. It also receives data back from the pump in reservoir implant 140 which may be viewed by the patient and stored for retransmission to the medical provider software application 120, thus allowing the patient to transdermally activate, control and power the implant and for the medical provider to reprogram and monitor implant usage and performance, respectively.

Figure 3A:
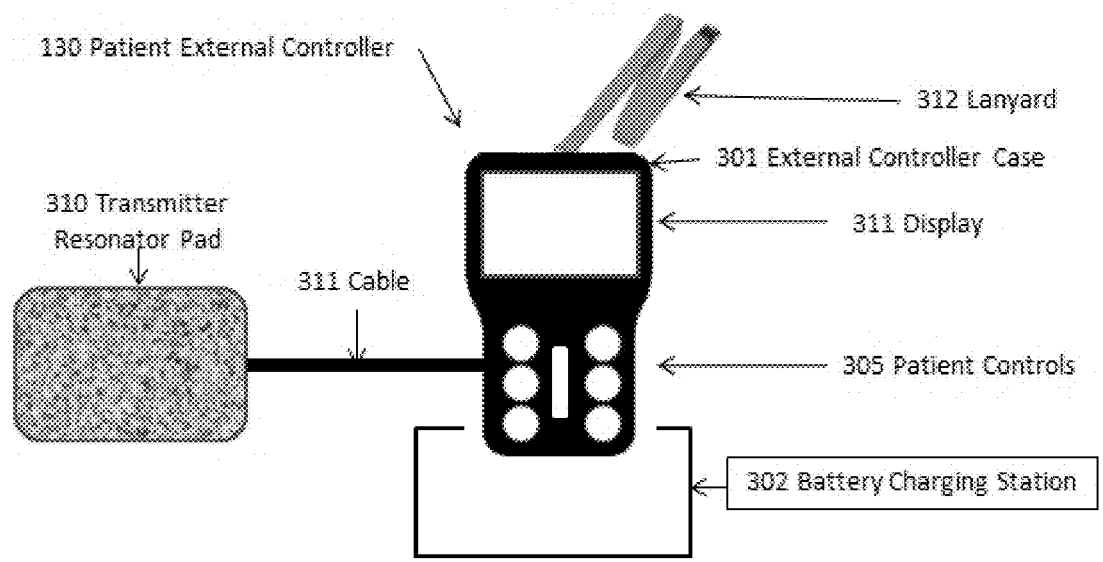
FIG. 3A is an illustration of an example patient external controller.

FIG. 3A illustrates an example of a hand-held patient external controller. As shown in the Figure, the patient external controller includes an external controller case 301 with a touch screen display 311 and patient control 305 buttons. Patient controls 305 may be provided via push buttons, a touch screen display 311 or both. They may include "On, Off, Inflate, and Deflate." Multiple controls are provided for implants operating more than one inflatable medical implant 150. For example, the buttons may control inflation and deflation of three inflatable medical implants 150. The center button is a "Power On and Off" button. The patient external controller 130 may also have a lanyard 312 which allows patients to hang the controller from the neck while in use. In operation, the patient may place the external controller case 301 or the transmitter resonator pad 310 on, or in proximity to, the dermis 101, over the pump in reservoir implant 140, and then operate the desired patient control 305.

Figure 3B:
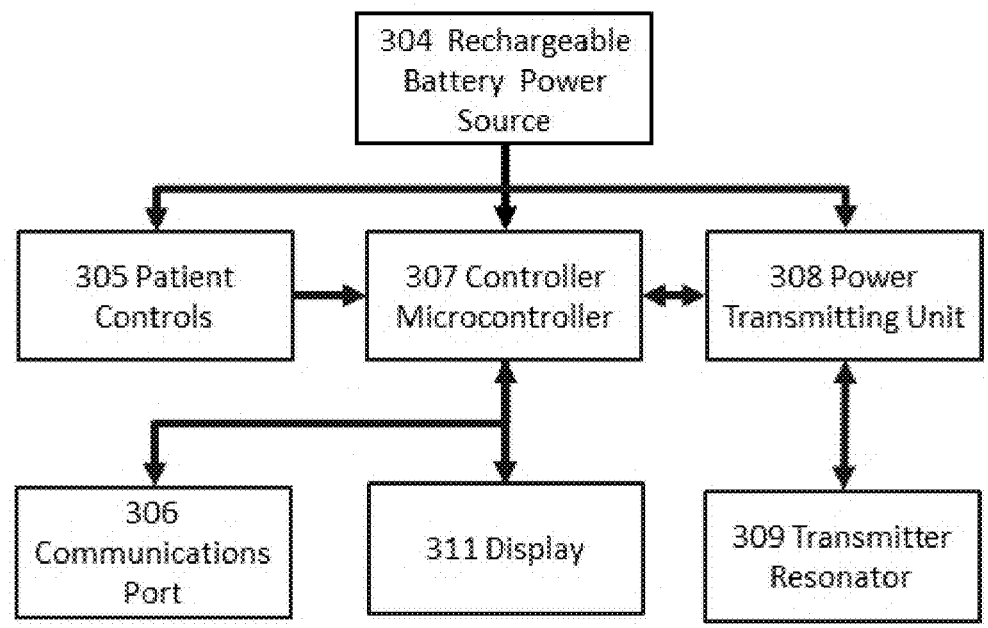
FIG. 3B is a block diagram representation of the components of the patient external controller's electronic circuitry.

FIG. 3B is a block diagram representation of the patient external controller's 130 electronic circuitry. It contains a rechargeable battery power source 304, such as Lithium Ion or Nickel Metal Hydride batteries, to power the apparatus. When not in use, the patient external controller 130 may sit in a battery charging station 302, which provides direct current power to charge the rechargeable battery power source 304. Overcurrent, short circuit and over temperature protection may be provided. The battery charging station 302 may be powered from 120-220 volt (V), 50-60 hertz (Hz) wall outlet connections or 12 V storage batteries.

When the "On" patient control 305 is selected, the rechargeable battery power source 304 supplies power to the patient external controller 130 to energize its functions and await commands from the patient via patient controls 305 or from the medical provider via the communications port 306. Upon activating another control, a signal is sent to a controller microcontroller 307, such as a TMS 320 series microcontroller, which contains a nonvolatile memory for storing its executable computer instructions, medical provider's settings, and implants usage data, to institute and control apparatus actions. Should an action include operation of the pump in reservoir implant 140, a handshake is first conducted with the pump in reservoir implant 140 over the bidirectional communications link 132 to ensure it is ready for operation, and foreign object detection is initiated for safety.

Here, the controller microcontroller 307, connected to the power transmitting unit 308 over a standard bus, such as an I²C serial interface bus, sends handshake messages to the power transmitting unit 308 for transmission through the transmitter resonator 309 to pump in reservoir implant 140. Proper messages must be received back from the pump in reservoir implant 140 for the action to continue. The controller microcontroller 307 may be programmed to stop operation if the bidirectional communications link 132 signal is lost, a preset pump in reservoir implant 140 safety parameter is exceeded, or a foreign object is detected. The controller microcontroller 307 may turn off power if no patient control 305 is received after a preset time interval.

Upon completion of the handshake and safety checks, the power transmitting unit 308 generates and transmits evanescent radio frequency transdermal power 131 via a transmitting resonator 309 to the pump in reservoir implant 130, and may operate in the 6 MHz to 7 MHz band, a decade below the 63.87 MHz radio frequency of 1.5 tesla MRI machines.

As shown in FIG. 1, evanescent power transmission 131 may be used to transmit power to the pump in reservoir implant 140, as opposed to a close-coupled magnetic induction power transmission, because it provides more efficient, longer distance, higher power operation at a lower voltage. The transmitter resonator 309 may transmit over 5 watts of power, across more than 2-inchs of dermis 101, tissue and fat, to the pump in reservoir implant 140.

The transmitter resonator 309 includes a wire coil and a matching capacitor network combination which resonates at the desired transmission frequency, such as 6.78 MHz. Wired coils may be located in both the patient external controller case 301 and in the transmitter resonator pad 310, which may make it easier for the patient to hold the wire coil on the skin over the implant. The transmitter resonator pad 310 may connect to the external controller case 301 via a plugin cable 311. Plugging the cable 311 into the external controller case 301 disconnects the case's wire coil.

As shown in FIG. 1, the pump in reservoir implant 140 includes an outer flexible reservoir case 141, which may be elliptical in shape and hold isotonic fluid 145 as the working fluid for inflatable medical implants 150. As noted, the inflatable medical implants may be penile cylinder implants, urethra cuff implants or anal cuff implants. The amount of isotonic fluid may depend on the implant and desired use. For example, 75 milliliters of isotonic fluid may be used with a penile cylinder implant.

The pump in reservoir implant 140 further includes a pump package 142, which may be in the form of a cylinder, 55 millimeters in diameter by 45 millimeters long and submerged in the isotonic fluid 145. A flexible tube 144 with a connector 146 carries the isotonic fluid 145 to and from inflatable medical implants 150. A pressure relief tube 143 is also included, should the apparatus fail.

The reservoir case 141 may have a biologically inert outer wall with an insulating material, such as Nomex, molded into the wall to reduce heat transfer rate from the isotonic fluid to the patient during low duty cycle inflation and deflation. The unfilled reservoir may be folded into a cylindrical shape to ease insertion by the surgeon. The surgeon may insert the reservoir case 141 into the patient's abdomen 102 and then fill it with isotonic fluid 145. The isotonic fluid 145 is the pump's operating fluid, provides a heat sink for the pump package 142, and does not change the patient's local electrolytic balance should leakage occur.

Figure 4A:
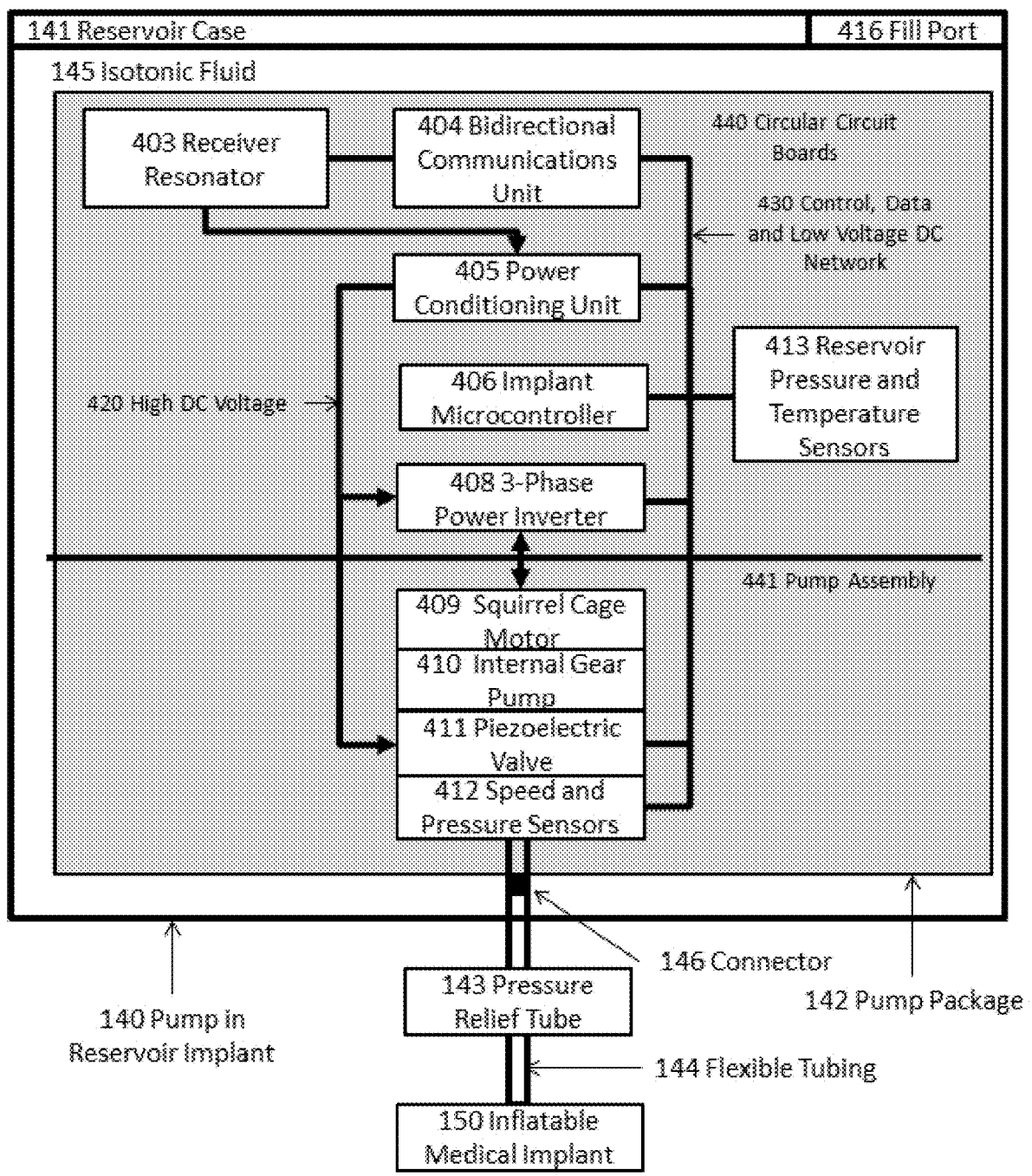
FIG. 4A shows a diagram of an MR-Conditional pump in reservoir implant operating a single inflatable medical implant.
Figure 4B:
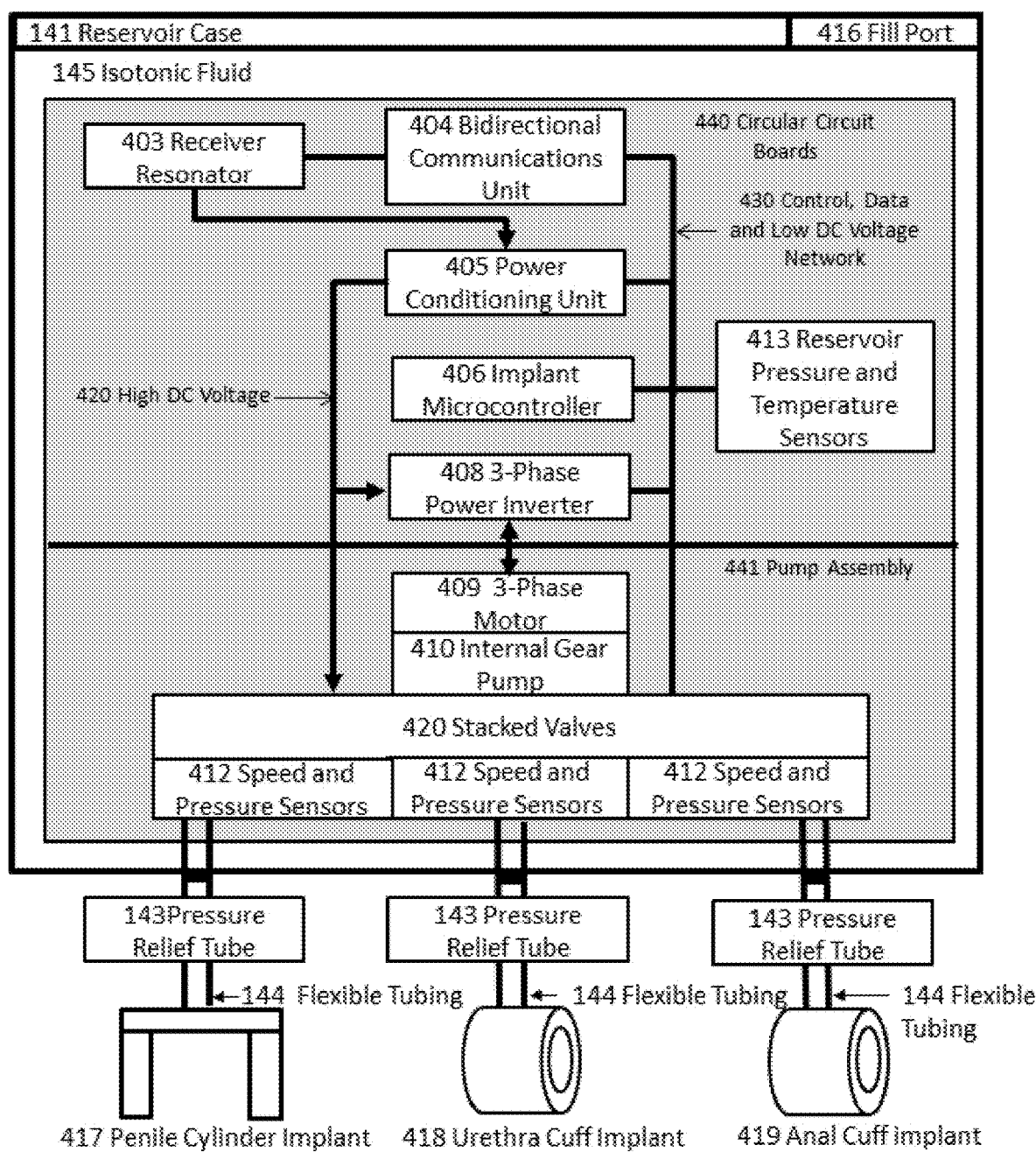
FIG. 4B shows a diagram of an MR-Conditional pump in reservoir implant operating three inflatable medical implants.
Figure 6:
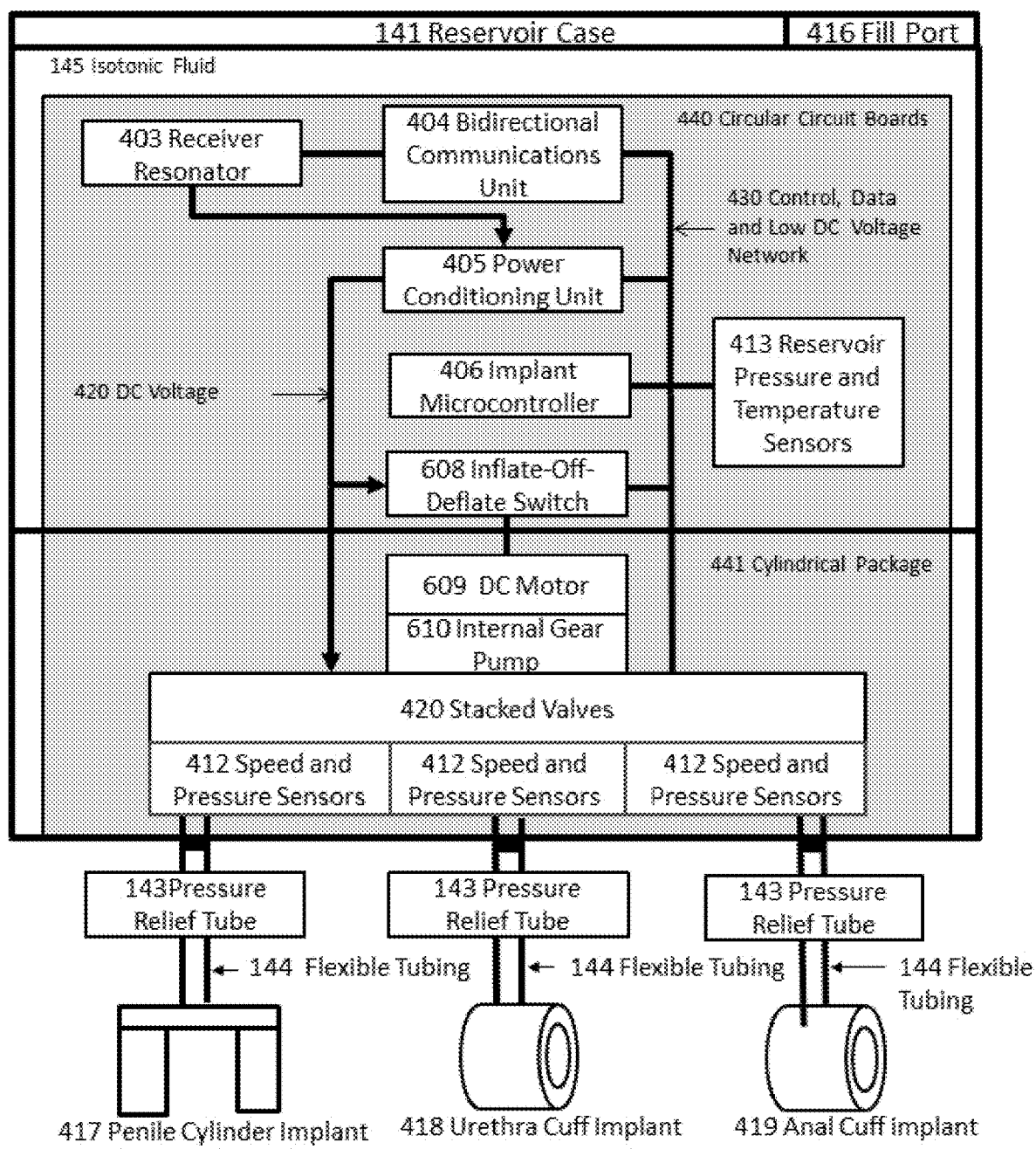
FIG. 6 shows an MR-Unsafe pump in reservoir implant operating three inflatable medical implants.

As shown in FIGS. 4A, 4B and 6, the apparatus may inflate and deflate any combination of penile cylinder implants 417, urethra cuff implants 418, anal cuff implants 419, and other inflatable medical implants. FIG. 4A illustrates a pump in reservoir implant 140 operating a single inflatable medical implant 150. FIG. 4B shows a pump in reservoir implant 140 operating three inflatable medical implants: a penile cylinder implant 417, a urethra cuff implant 418, and an anal cuff implant 419.

The pump in reservoir implant 140 may be MR-Conditional or MR-Safe, with components that may not translate, rotate, excessively heat or cause MRI picture distortion when introduced into certain MRI machines. As shown in FIG. 6, the pump in reservoir implant 140 may also be implemented with components which contain MR-Unsafe ferrous materials.

The MR-Safe or MR-Conditional pump in reservoir implant 140 apparatus may inflate and deflate penile cylinder implants 417. In order to inflate and deflate the implants quickly, the pump may pump 60 milliliters of fluid at 25 pounds per square inch pressure in 45 seconds, which includes a safety factor. Pumping equations show that this is equivalent to providing 0.23 watts of pumping power at the penile cylinder implant 417. Since cuffs require less than $\frac{1}{10}^{th}$ the amount of fluid transfer than for cylinders, requirements are less stringent for these implants.

MR-Unsafe ferrous brushed direct current and brushless direct current electric motors coupled to ferrous containing positive displacement internal gear pumps, which meet these requirements, may be used. These motors use ferrous materials to greatly increase torque by linking magnetic flux between the motor's stator and rotor such that very little leakage flux is generated. For such motors, removing ferrous materials for MRI safety reduces flux linkages, thereby greatly reducing torque and power output. In such motors, some torque can be bought back by increasing motor diameter and applied voltage. However, minimizing these parameters is desirable.

Furthermore, for positive displacement rotary internal gear pumps, dynamic sealing allows the gears to move while maintaining separation between the pump's inlet and outlet. These dynamic seals are maintained as the gears rotate. However, there must be some clearances for the gears to move. These clearances allow fluid to leak back from the high-pressure outlet to the low-pressure inlet, thereby reducing pump efficiency, especially at low pump output pressures, such as 25 pounds per square inch, and will cause fluid leakage back and forth between the reservoir case 141 and the inflatable medical implant 150 even when the pump is not in operation.

A nonferrous combination of a 3-phase squirrel cage motor and positive displacement internal gear pump may also be used. For example, a 50,000 revolutions per minute motor, reduction gear and low speed pump combination, 10 millimeters in diameter, may be used. To maximize motor-pump efficiency and minimize motor diameter without using reduction gears with their efficiency loss, a nonferrous 50 millimeter diameter squirrel cage motor 409, operating at 4000 revolutions per minute, power by a 24 volt direct current input 3-phase power inverter 408 and driving a 10 millimeter diameter nonferrous positive displacement internal gear pump 410 may be used.

An electrically operated, nonferrous piezoelectric valve 411 may be added at the internal gear pump 410 connection with the inflatable medical implant 150 to prevent fluid leakage back to the reservoir through the pump, and vice versa. Individually operating a stack of such valves allows a single motor and pump to operate multiple inflatable medical implants, providing a significant cost and size saving. Less than 5 watts of transdermal power is needed to power the pump in reservoir implant.

Details of the pump in reservoir implant 140 operating a single inflatable medical implant 150 are shown in FIG. 4A. In the figure, a reservoir case 141 contains a pump package 142 which includes a transdermal power receiver resonator 403; electrical components mounted on circular circuit boards 440; a nonferrous pump assembly, comprising a 3-phase squirrel cage motor 409, an internal gear pump 410, a piezoelectric valve 411; and pump speed and pressure sensors 412, all submerged in an isotonic fluid 145.

Figure 5A:
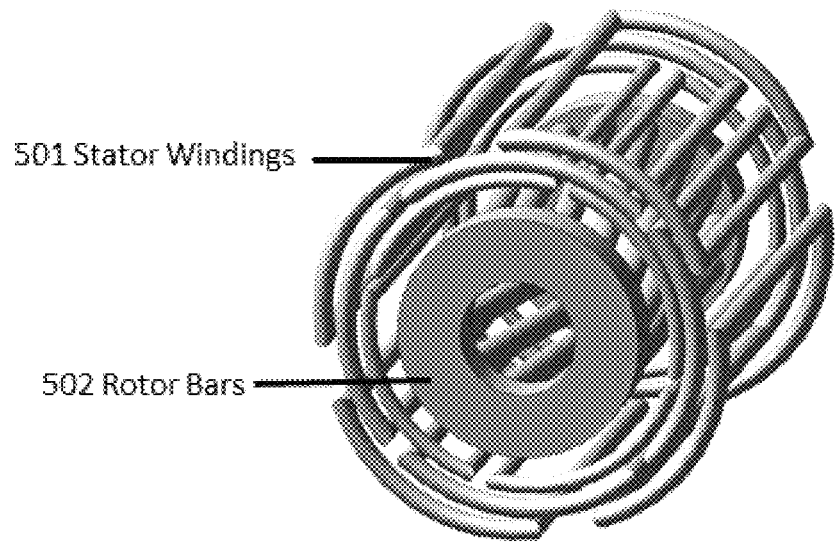
FIG. 5A shows the windings of a nonferrous 4-pole squirrel cage motor.
Figure 5B:
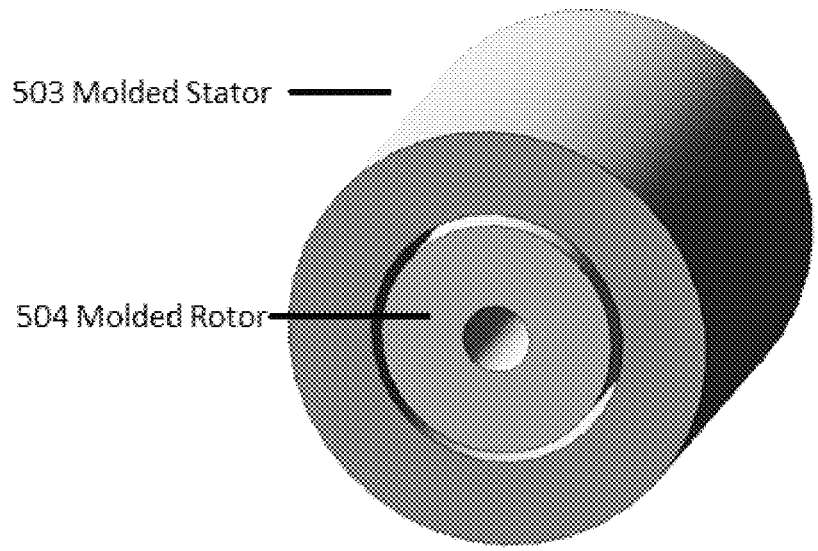
FIG. 5B shows a nonferrous 4-pole squirrel cage motor with the rotor and stator encapsulated.

FIGS. 5A and 5B illustrate a squirrel cage motor, supplied with 3-phase alternating current power, and able to be operated at various speeds. For example, a 50 millimeter diameter by 25 millimeter long, 3-phase 4-pole squirrel cage motor, supplied with 3-phase 14.9 volts alternating current power, and operating at 4,000 revolutions per minute, may be used. FIG. 5A shows the motor's 4-pole stator windings 501 and the rotor bars 502 with their short circuiting endplates. In FIG. 5B, the stator windings 501 and the rotor bars 502 are encapsulated in molded plastic to reduce windage losses and to stabilize the rotor under centrifugal force. A 3-phase squirrel cage motor has the advantages of small size, self-starting, high speed operation. Squirrel cage motors do not use brushes or slip rings, wear items which reduce motor life.

Figure 8:
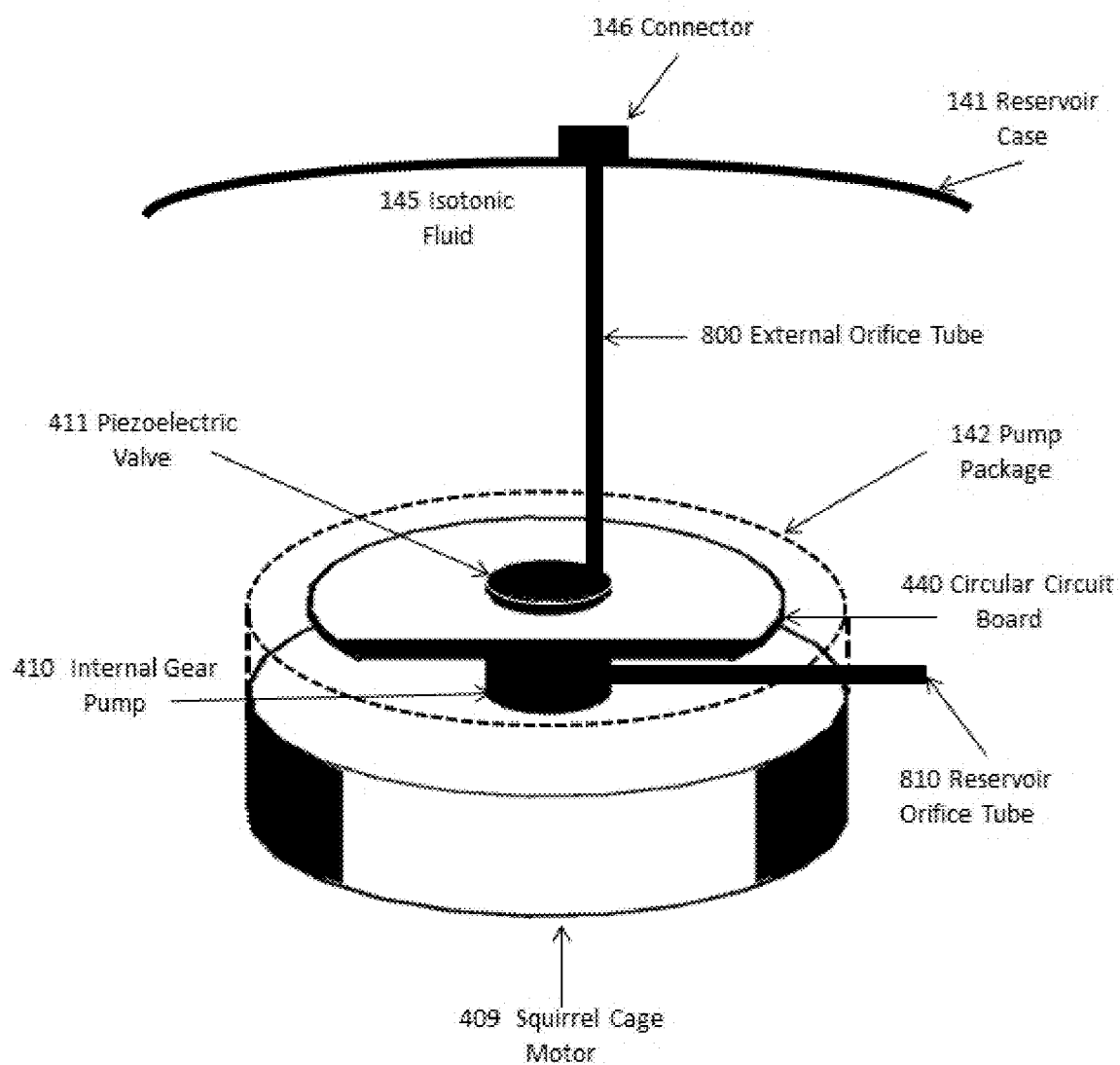
FIG. 8 shows a pump package illustrating the circuit board, pump and valve arrangement.

As shown in FIG. 4A and FIG. 8, the submerged squirrel cage motor 409 drives a submerged nonferrous, positive displacement rotary internal gear pump 410, where one pump orifice is open to the reservoir through the reservoir orifice tube 810. The nonferrous internal gear pump may be 10 millimeters in diameter and 10 millimeters long and have shaft seals to prevent fluid from entering the squirrel cage motor 409.

The other internal gear pump 410 orifice may be assembled to a 10 millimeter diameter nonferrous piezoelectric valve 411 orifice. The valve is closed when not in use to prevent leakage of fluid through the internal gear pump 410.

An external orifice tube 800 connects the piezoelectric valve's 411 other orifice to a connector 146 placed through the reservoir case 141 for attachment of the flexible tube 144 during surgery when the surgeon threads the flexible tube 144 from the reservoir case 141 to the inflatable medical implant 150 and connects it to the pump in reservoir implant using connector 146.

FIG. 4B shows individually controlled piezoelectric stacked valves 420 operating three implants: a dual penile cylinder implant 417, a urethra cuff implant 418 and an anal cuff implant 419. A computer interlock is provided so only one valve can be open at a time.

Implant electronics driving the pump 441, may be housed on military-grade, multilayer, coated circular circuit boards 440 for physical damage and short circuit protection and moisture-proofing. As shown in FIG. 8, the circular circuit boards 440 may be 50 millimeters in diameter and have holes in their centers for placement around the 10 millimeter diameter internal gear pump 410 and piezoelectric valve 411. The boards and their components are, at least, MR-Conditional and may be MR-Safe.

Figure 7:
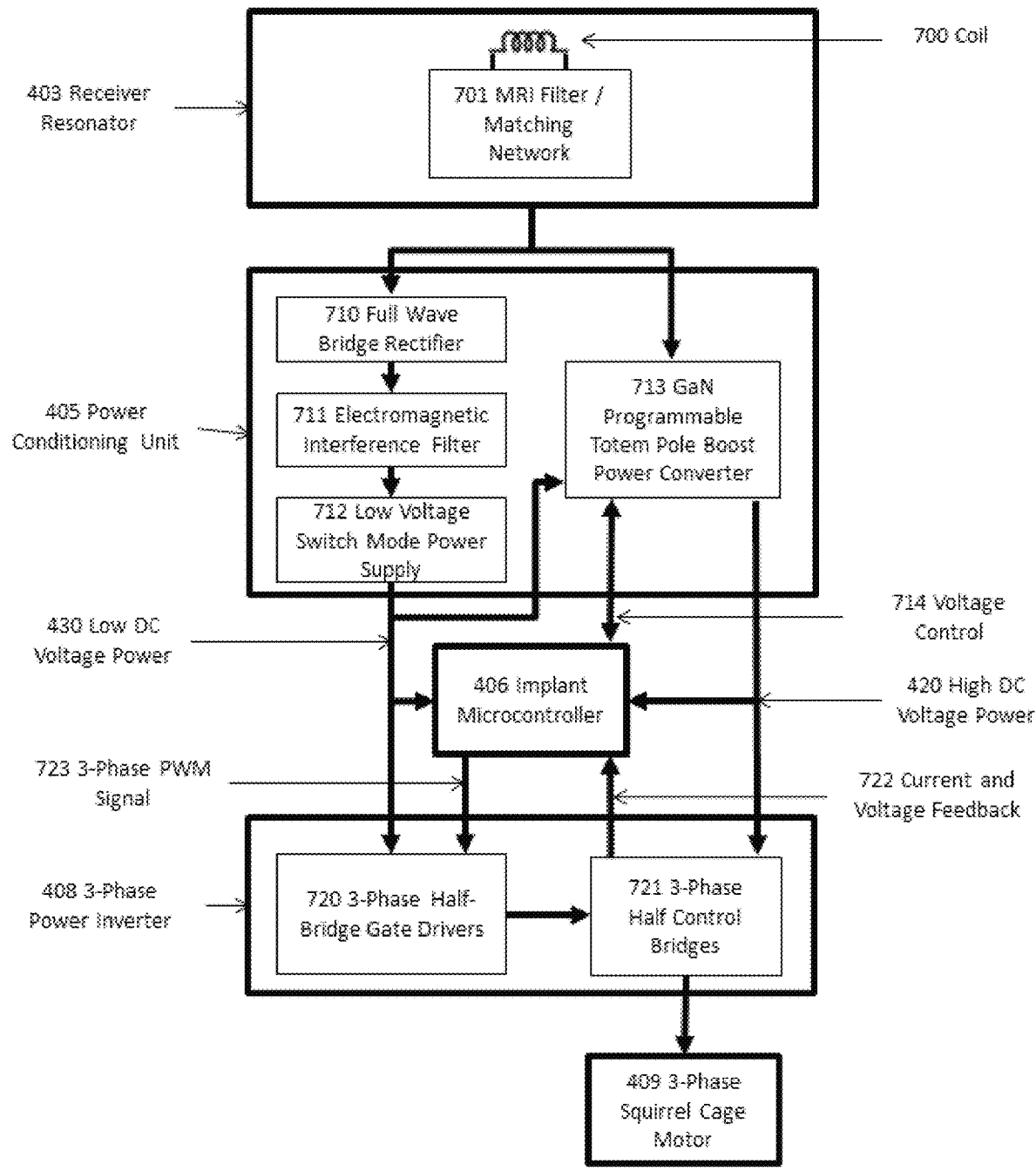
FIG. 7 shows a block diagram of power electronics that may be used in the inflatable medical implant system.

As shown in FIG. 7 and FIG. 4A, the receive resonator 403 may receive evanescent power transmissions 131 transdermally from the transmitting resonator 309. Additionally, it may be used for the bidirectional communication link 132 with the patient external controller 130. The bidirectional communications unit 404 codes and decodes these bidirectional signals for the implant microcontroller 406.

The receiver resonator 403 includes a resonant circuit made up of an nonferrous wire coil 700 inductor, which may be in the shape of a 45 millimeter diameter circle, and a MRI filter/matching network 701, which may resonate at 6.78 MHz and filter out the higher frequency transmissions of MRI machines, such as 63.9 MHz from 1.5 tesla MRI machines. The wire coil 700 may be etched onto the circular circuit board 440, molded into the reservoir case 141, or housed in a separate case which, in obese patients, may be located under the dermis 101. The receiver resonator's 403 output voltage may vary widely from patient to patient with placement of the transmitter resonator 309 with respect to coil 700.

The receiver resonator 403 feeds alternating current power to a power conditioning unit 405, which converts the varying received alternating current voltage to stable direct current voltages for the electronics, motor and sensors. First, a low power low voltage power supply may generate 5 volts direct current to power the electronic components and sensors. The power conditioning unit 405 may use Schottky diodes in a full wave bridge rectifier 710 configuration to convert the alternating current voltage into direct current. An electromagnetic interference filter 711 is applied to remove diode switching transient noise.

Since the electromagnetic interference filtered 711 output voltage can vary widely, a low voltage switch mode power supply 712 may provide stable 5 volts direct current. The low voltage switch mode power supply 712 may contain an under voltage-over voltage protection circuit which only energizes the switch mode power supply when appropriate direct current voltage appears at its input to produce its desired output. Switch mode power supplies obviate the need for inefficient linear regulators and are more efficient than voltage feedback loops to the patient external controller 130.

Upon reception of power from the low voltage switch mode power supply 712, an implant microcontroller 406 is energized, does a handshake with the patient external controller 130 and self-tests for problems in the pump in reservoir implant 130, such as out of range temperature and pressure and electric current leakage. The implant microcontroller 406 then sends status data back to the patient external controller 130, which, if all is well, energizes the patient controls 305.

The implant microcontroller 406, such as a MR-Safe MSP430 or C2000 series microcontroller, may contain an encrypted nonvolatile memory, a reduced instruction set computer, a pulse width modulation unit, at least one analog-to-digital converter, at least one data bus, and self-test capability.

Upon reception of inflation or deflation signals and data from the patient external controller 130, the implant microprocessor 406 may turn on a gallium nitride transistor, programmable totem pole boost power converter 713 to generate stable high voltage direct current 140, such as 24 volts direct current. The gallium nitride transistor, programmable totem pole power converter 713 uses gallium nitride high electron mobility field effect transistor switches, which achieve lower losses than silicon-based components, to nominally provide 24 volts direct current to power the 3-power inverter 408 for the 3-phase squirrel cage motor 409. The gallium nitride transistor, totem pole boost power converter 713 operates at a lower input voltage, such as 12 volts direct current, than its output voltage, thereby allowing for lower evanescent power transmission 131 voltage from a lower voltage rechargeable battery power source 304, for example 12 volts direct current, in the patient external controller 130, which results in less cost and greater patient safety.

The implant microcontroller 406 uses the pulse width modulation voltage control 714 path to sense the alternating current input voltage, determines when that voltage crosses zero and then sends pulse width modulation signals to turn on and turn off gallium nitride half-bridge transistors in an inductive boost converter configuration to achieve alternating current to direct current boost conversion to provide the high direct current voltage power 420. The high direct current voltage power 420 voltage is fed back to the implant microprocessor 406 for closed loop control of the voltage by varying the pulse width modulation.

The high voltage direct current 420 output of the gallium nitride transistor, programmable totem pole power converter 713 is then inverted to 3-phase alternating current by a 3-phase power inverter 408 controlled by the implant microcontroller 406. The frequency and the number of sinusoidal cycles to be generated may be set from the medical provider software application 120. For a 4-pole, 4000 revolution per minute squirrel cage motor, the implant microcontroller 406's pulse width modulation unit, operating at 50 KHz, may generate three 200 Hz pulse width modulation sinusoids set 120 degrees apart for low harmonic distortion losses. Soft pulse width modulation gallium nitride transistor startup is used to decrease losses from transistor switching transients. Motor direction, and therefore inflatable medical implant 150 inflation or deflation, is achieved by switching two phases of the three 3-phase signals.

The sinusoidal pulse width modulation signals are input to three 3-phase half-bridge gate drivers 720, which, in turn, drive three 3-phase half control bridges 721, to generate 3-phase power to drive the motor. Current and voltage feedback 722 from the 3-phase half control bridges 721 is used in the implant microcontroller 406 to provide stable operation of this nonferrous low stator impedance motor, and detect faults for safe operation.

In operation, the motor, which drives the pump, sees a varying load. At the start of the pumping cycle, the pump sees high pressure at its input and low pressures is at its output and requires reduced motor torque, and therefore power, to operate. At the end of the cycle, the opposite is true. Efficiency of the pump and motor combination is achieved by calculating and applying the optimum 3-phase voltage at the optimum 3-phase frequency continuously over the pumping cycle. This optimization may be achieved by the implant microprocessor 406 using the pulse width modulation voltage control 714 feedback loop and the current and voltage feedback 722 loop to set the high direct current voltage 420 and the 3-Phase pulse width modulation signal 723 to control the 3-phase squirrel cage motor's 409 speed and torque.

Alternatively, the gallium nitride transistor, programmable totem pole boost power converter 713 may be replaced by a Schottky diode full wave bridge rectifier and electromagnetic interference filter, and the varying high direct current voltage power 420 is fed directly to the 3-phase half control bridges 721, which act as both a voltage regulator and a direct current to alternating current inverter. The implant microprocessor then generates the correct pulse width modulation signals for the varying high direct current voltage power 420 when it computes the pulse width modulation signals for the 3-phase squirrel cage motor 409. Additionally it provides over and under voltage protection for the varying high direct current voltage power 420.

The implant microcontroller 406 also receives, processes, and formats implant performance and safety data for transmission to the patient external controller 130. In some implementations, additional analog-to-digital and digital-to-analog integrated circuit are necessary to handle all the sensor data.

Pump pressure and motor speed sensors 412 are provided along with reservoir pressure and temperature sensors 414. Pressure and speed data is sent to the implant microcontroller 406. The pressure and speed data may be used for automatic cutoff should the pump run over or under speed limits, or on the occurrence of leakage, over inflation or a fluid blockage.

The pressure and speed data may also be used to help the medical provider set the amount of fluid to be transferred that is best suited for the patient. Reservoir pressure and temperature sensors 413 may be included on the circular circuit boards 440 to send pressure and temperature data to the implant microcontroller 406 for high temperature cutoff should the isotonic fluid 145 overheat. Additionally, integrated circuit chips used in the power receiving unit 405 and implant microcontroller 406 may have internal temperatures sensors that turn off the chip in over temperature situations.

Should the apparatus fail with an inflatable medical implant 150, such as a penile cylinder implant 417, inflated, a pressure relief tube 143 is provided to allow medical providers to manually deflate the inflatable medical implant 150 by inserting a small bore hypodermic needle into the pressure relief tube 143 and draw out the inflating fluid. One end of the tube is located at the inflatable medical implant 150 and the other end just below the dermis 101.

FIG. 6 shows a diagram of a MR-Unsafe pump in reservoir implant implementation. The implementation of FIG. 6 includes many of the same components already described in FIGS. 4A and 4B. However, in FIG. 6, the 3-phase power inverter and nonferrous pump and motor 408, 409, 410, from FIGS. 4A and 4B are replaced by an inflate-off-deflate switch 608, direct current motor 609 and internal gear pump 610.

Coupling between the direct current motor 609 and the internal gear pump 610 may be magnetic, allowing the pump to be in submerged in the isotonic fluid 145 without the need for seals in the pump, thereby increasing efficiency and reliability. Also, the 3-phase power inverter 408 is replaced by connecting the 713 gallium nitride transistor, programmable totem pole boost power converter's 713 high direct current voltage power 420 through an implant microcontroller 406 controlled half-bridge reversing direct current power control inflate-off-deflate switch 608, to turn the motor on and off and to reverse its direction.

FIG. 8 shows the pump package 142 illustrating the circular circuit board 440, squirrel cage motor 409 and piezoelectric valve 411 arrangement. In the pump package 142, an internal gear pump orifice 410 directly connects to a piezoelectric valve 411 orifice. A reservoir orifice tube 810 then connects the other internal gear pump 410 orifice to inside the reservoir case 141 in contact with the isotonic fluid 145. An external orifice tube 800 connects the other piezoelectric valve's 411 orifice to a connector 146 leading outside of the reservoir case 141. The figure also shows a single circular circuit board 440 mounted around a piezoelectric valve 411.

As an added benefit to pumping fluid to inflate and deflate inflatable medical implants, this apparatus may provide vibrating penile cylinder implants 417 by modulating the implant microcontroller's 406 3-phase pulse width modulation signal, or by adding a pressure transducer and audio power amplifier (not shown) in fluid communications with an inflatable penile implant's input flexible tube.

The invention claimed is:

1. A pump in reservoir implant for inflating inflatable medical implants comprising:
   at least one nonferrous motor;
   a nonferrous fluid pump connected to the at least one nonferrous motor; and
   at least one nonferrous valve connected to the nonferrous fluid pump, configured to allow fluid to pass from the pump to an inflatable medical implant.

2. The pump in reservoir implant of claim 1, wherein the at least one nonferrous motor includes a 3-phase nonferrous induction or synchronous motor, wherein the nonferrous fluid pump includes a nonferrous gear pump; and
   wherein the at least one nonferrous valve includes multiple, independently electrically controlled nonferrous fluid valves.

3. The pump in reservoir implant of claim 1, further comprising multiple independently controlled valves configured to be connected to multiple inflatable implants.

4. The pump in reservoir implant of claim 1, wherein the pump is configured to inflate or deflate the inflatable medical implant.

* * * * *